US 6,853,454 B1

(12) United States Patent
Heffelfinger

(10) Patent No.: US 6,853,454 B1
(45) Date of Patent: Feb. 8, 2005

(54) OPTICAL ANALYSIS SYSTEMS

(75) Inventor: David M. Heffelfinger, Sequim, WA (US)

(73) Assignee: Alpha Innotech Corporation, San Leandro, CA (US)

( * ) Notice: Subject to any disclaimer, the term of this patent is extended or adjusted under 35 U.S.C. 154(b) by 0 days.

(21) Appl. No.: 10/758,576

(22) Filed: Jan. 15, 2004

(51) Int. Cl.$^7$ .............................................. G01N 21/47
(52) U.S. Cl. ...................... 356/446; 356/394; 356/398; 259/559.31; 382/103
(58) Field of Search ............................... 356/445–448, 356/601, 614, 629–630, 388–398; 250/559.21, 559.31, 559.38; 382/100, 103

(56) References Cited

U.S. PATENT DOCUMENTS

| | | | |
|---|---|---|---|
| 5,091,652 A | 2/1992 | Mathies et al. ........... 250/458.1 |
| 5,173,748 A | 12/1992 | Bilhorn ...................... 356/328 |
| 5,192,980 A | 3/1993 | Dixon et al. ................ 356/326 |
| 5,517,312 A | * 5/1996 | Finarov ...................... 356/630 |
| 5,547,849 A | 8/1996 | Baer et al. ................. 435/7.24 |
| 5,585,639 A | 12/1996 | Dorsel et al. ............. 250/458.1 |
| 5,587,832 A | 12/1996 | Krause ....................... 359/385 |
| 5,892,539 A | 4/1999 | Colvin ......................... 348/80 |
| 5,989,835 A | 11/1999 | Dunlay et al. ............... 435/7.2 |
| 6,122,078 A | 9/2000 | Leberl et al. ............... 358/474 |
| 6,124,934 A | * 9/2000 | Shahar et al. ............... 356/624 |
| 6,130,427 A | 10/2000 | Park et al. ................... 250/306 |
| 6,130,745 A | 10/2000 | Manian et al. .............. 356/123 |
| 6,147,798 A | 11/2000 | Brooker et al. ............. 359/368 |
| 6,271,042 B1 | 8/2001 | Watson, Jr. et al. ........ 436/172 |
| 6,365,367 B1 | 4/2002 | Friedman et al. ............. 435/29 |
| 6,426,835 B1 | 7/2002 | Endo et al. ................. 359/388 |
| 6,441,894 B1 | 8/2002 | Manian et al. .............. 356/123 |
| 6,483,641 B1 | 11/2002 | MacAulay ................... 359/385 |
| 6,573,039 B1 | 6/2003 | Dunlay et al. ................. 435/4 |
| 6,590,703 B2 | 7/2003 | Park et al. .................. 359/372 |
| 6,727,987 B2 | * 4/2004 | Yonezawa ................. 356/237.2 |

OTHER PUBLICATIONS

Richard P. ughland, "Handbook of Fluorescent Probes and Research Chemicals", Molecular Probes, 6$^{th}$ edition, chapter 19—"Photoactivatable (Caged) Probes", pp. 447–456.

* cited by examiner

Primary Examiner—Gregory J. Toatley, Jr.
Assistant Examiner—Sang H Nguyen
(74) Attorney, Agent, or Firm—Schneck & Schneck; Thomas Schneck; David M. Schneck

(57) ABSTRACT

A system for optical detection of kinetic samples. The system includes a dual set of detectors linked to a single processor. The time of signal integration is different for each detector, allowing one detector to have a higher sensitivity by integrating over a longer time period while the second detector using shorter integration periods is able to measure kinetic events.

11 Claims, 8 Drawing Sheets

OPTICAL ANALYSIS SYSTEMS

TECHNICAL FIELD

This invention relates to optical analysis systems and specifically to systems that image onto area array detectors.

BACKGROUND ART

All references disclosed below are hereby incorporated by reference herein.

The recent sequencing of the human genome have led to the identification of a large number of human gene sequences and sequence variation. Current efforts in proteomics are leading to the identification of the entire complement of proteins in a cell or organism. These developments have produced a wide variety of targets for biological inquiry. For example, numerous assays are carried out in microplate wells. One assay may be effected in each well. Assay reaction may be determined by an optically detectable change. The well density presently available in standard 8×12 cm microplates ranges from 96 wells to 1536 well plates. The diameter of the well bottom detected may range from a few millimeters to fractions of a millimeter, depending on the assay and well density.

In investigating genes, cells and proteins a number of biological techniques is employed requiring a diverse range of instrumentation.

One example of biological technique to analyze nucleic acids and proteins has been gel separation. Nucleic acids and proteins may be electrophoretically separated on gel, such as an agarose or acrylamide gel. The gels may be directly imaged on an area array detector using a stain to label bands of differing molecular weight.

Alternatively, the gels may be blotted onto a membrane and the membrane optically analyzed to detect the protein or nucleic acid sequence. Such separations may include localized separated samples having a wide variety of diameters. Optical systems for imaging gels may have a resolution of 200 to 25 microns to detect targets having a dimension of a millimeter or less. 50 micron resolution for gel targets are common. Optical systems imaging blots may have a resolution selected to image targets 2 millimeter or less. Generally a unique optical system is required for the imaging of such targets.

DNA arrays have emerged as a technology for investigating gene expression and variation. Oligonucleotides may be printed on a impermeable substrate such as a glass slide or the bottom of a well of a multiwell plate. Following hybridization with DNA fragments in a sample the spots or the array may be analyzed to detect hybridization of complimentary strands.

The nucleic acids are printed on the substrate at high densities minimizing the amount of reagents and samples required to effect an assay. A nucleic acid spot on array may be 1 to 100 microns in diameter. Presently a number of dedicated array readers are used for the analysis of nucleic acid arrays. One such system is disclosed in U.S. Pat. No. 5,585,639. In this system a focused illumination beam is scanned over an array and imaged onto a linear detector.

Cells are another biological target of interest. Cells have become an increasing interest as targets in ordered cell arrays. In one type of cell array, plasmids from a plasmid library are bonded to a glass slide. Each plasmid includes encoding cDNA regulated by a eucaryotic expression promoter. Using presently available technology for spotting nucleic acids onto a solid substrate, plasmids may be spotted on the slide at very high densities. Cells are deposited on top of the bonded plasmids. The plasmids are chemically transfected into the cells creating an array of spots of living cells. The cells at each spot express the gene present in the plasmid.

A variety of assays may be effected on the cells in a cell array. These assays include immunologic, histo-chemical, and functional assays. The plasmid libraries used to produce cell arrays may include a variety of different genes, or could include variants of the same gene. Cell arrays provide the opportunity to assay living cells, allowing the function and kinetics of proteins to be investigated. Such cell arrays could be used to express and characterize varied types of proteins. Even complex proteins, such as G-protein coupled receptors, ion channels, and membrane transport proteins could be functionally expressed in cell arrays. In one present assay cell arrays expressing variants of the HIV envelope protein are being investigated for structure, structural correlation with an individual's immune response, and functional interaction with receptors.

Cells and cell-sized targets (such as microbeads) are also commonly assayed in non-ordered formats. For example, cells in a liquid suspension may be added to a microplate well. The cells settle to the bottom of the well, forming a disordered two dimensional array. The cells analyzed may be 2 microns to 10 microns in diameter. Again, both cell arrays and their cell analysis systems have used dedicated optical instrumentation for the analysis of these targets. For intra-cellular imaging (e.g. cell nucleus or organelles) a resolution of 0.2 to 1 microns are needed.

A variety of different detection systems for cell imaging are available.

One type of cell analysis systems are laser-based scanners. Confocal laser imaging systems are disclosed in U.S. Pat. Nos. 6,147,798; 5,091,652; and 5,192,980. Volumetric laser cytometers are disclosed in U.S. Pat. No. 5,547,849. Such scanners are highly sensitive and may be optimized to the specific geometry of a substrate, such as a slide. The illumination wavelength is limited to the wavelength specific to a laser. This may limit the choice of dyes or other fluorescent markers that may be used in a sample. Alternatively, multiple lasers could be used increasing the cost and complexity of imaging systems. Another drawback of such systems is the adverse effect on cell viability of laser scanning. The resolution of such systems are limited to a narrow range of magnifications, generally a single magnification level for dedicated targets such as cell arrays. Imaging using a focused laser spot requires pixel by pixel excitation and scanning. The pixels must be combined to form a "virtual" image. A final limitation is photo-bleaching of dyes by the intense laser light.

An alternative system for detection of cells in ordered or non-ordered arrays are microscope based imaging detectors. One such system is disclosed in U.S. Pat. Nos. 5,989,835 and 6,573,039. Such devices are commonly epi-fluorescence microscopes with white light illumination and CCD detection. Multiple illumination and emission filter combinations allow flexible dye choices, and the dyes may be optimized for higher resolution. However, the limited fields of view of these devices prevent the use of large format CCDs with these devices. Microscope objectives were developed for the aperture of the eye (7 mm) rather than for the larger aperture required of modern CCDs which can exceed 25 mm. Such systems use microscope objectives to allow for variable magnification. However, microscope objectives are not well matched to large format commercially available CCDs. Such systems also are not designed to process the large data sets created by multiple images.

FIG. 1 illustrates the primary elements of the prior art Alpha Array 7000™ produced by Alpha Innotech (San Leandro, Calif.). This system is one instrument for detection of array targets. Related optical systems are described in U.S. Pat. No. 6,271,042. This system includes an arc lamp illumination source 2 producing an illumination beam 22. Illumination beam 22 passes through an optical filter 26 on filter wheel 24. Filter 26 allows transmittal of a selected range of wavelengths of light. Light transmitted through filter 26 is focused into opening 28 of bifurcated optical fiber 3. Bifurcated optical fiber 3 transmits the illumination beam to condenser lens 15. Light passing through lens 15 impinges on the sample substrate 30. The sample substrate 30 is held on multi-position slide holder 6 mounted on sample stage 4. Stage 4 is movable along an X and Y axis, with 1 micron precision. Bifurcated optical fiber 3 allows off-axis illumination of sample.

The illumination light 22 is directed onto a sample on sample substrate 30. Targets upon sample substrate 30 such as a spot on an array, are illuminated. The illumination light excites fluorescent dyes producing fluorescent emission. The emitted light is collected by objective lens 13 which collimates the emission of light beam 40. The beam passes through a filter 17 on filter wheel 16. Filter wheel 16 allows rotation of a number of different filters into the path of collected light. A user selects an appropriate emission filter depending on the dye or dyes used in the assay. In this way scattered illumination light would be filtered out from the collected light. Because such filters work best in locations of parallel rays, the filter wheels 16 is located between objective lens 13 and imaging lens 12 at a position of parallel light rays. The collected light beam 40 passes through imaging lens 12 which focuses the image onto area array detector 11.

The optical configuration allows for a 15 micron resolution, which is sufficient to detect individual cells that are 30 to 50 microns in diameter. This resolution is not sufficient to image intracellular components, or parameterize or classify cells. The system has a 200 micron depth of field. The system also has a 20 millimeter range of focus. This focal range allows use of taller samples or sample containers, such as microplates. The detector used is 1.3 megapixel cooled charge coupled detector (CCD). This detector has 50% quantum efficiency at 400 nanometers and a 18000 electron quantum well.

The use of a cooled CCD for the detector allows for operation of the system using long integration periods. Long integration periods enhance sensitivity by allowing longer detection intervals during which time more collected light is measured. Alternatively shorter integration times may be used for kinetic studies. Such short integration times lower the sensitivity of detection. The individual image captured view of each CCD exposure may be combined using a cross correlation algorithm into a single mosaic image. At pixel resolution of 15 microns a single microscope slide can be read in 15 seconds and imaged in 5 views. This allows kinetic biological signals to be analyzed over minutes or hours.

The 0.13 numerical aperture lens system is designed to image onto the CCD detector. The lens selection is not based on a microscope objective, allowing for a larger aperture of 25 mm. This lens is selected for use at approximately 0.5 magnification to a large format 1.3 megapixel CCD. This lens also provides a sufficiently large working distance to accommodate the full height of a microplate.

While a number of separate imaging systems exist for specific dedicated targets, a need for more versatile imaging systems remains. The large diversity in the size of biological targets requires a system that has a broad range of magnification levels. Given that the target size may range from a 500 micron diameter target on a blot to a 0.5 micron diameter cell organelle the magnification ideally would span three orders of magnitude. Presently no system allows detection of such a range of target sizes. In addition, the optical aberrations of coma, distortion, and lateral color may be a significant limitation to the imaging capabilities of the system.

A number of currently available systems operate using microscope objective and imaging lens. Such lens are poorly adapted to presently available large format CCD array detectors. As such, the high optical magnification of a microscope objective must be de-magnified to fit such detectors. In addition the systems are often limited either by design of the optics or by design of stage to imaging to one specific type of substrate, such as slides or multiwell plates. This further limits the general utility of such systems and often requires dedicated systems for use with each substrate or sample type.

Typically, systems that use the optics of a microscope use on-axis illumination. As used herein, on-axis illumination means that the illumination light passes through the objective lens before striking the target. This is accomplished by use of a dichroic mirror to reflect the wavelengths of the illumination beam and pass wavelengths of the emitted light from the target. This type of illumination can produce an illumination beam that is highly non-uniform, and it can produce internal reflections that limit the sensitivity of the overall detection system. An alternative is to illuminate off-axis. As used herein, off-axis illumination means that the illumination beam does not pass through the objective lens before striking the target. When using off-axis illumination with a variable magnification system, it is most efficient to use optical means to vary the size of the illumination spot so as to match it to the field of view.

There is also a need to rapidly focus the optics on a substrate. In many systems autofocus is performed by moving the objective lens until the sample comes into focus. However, such relocation of the objective lens changes the magnification. Such a change in magnification makes tiling of views into one mosaic image much more difficult.

Cells provide unique challenges for an imaging system. For cell array applications ideally the cells should remain alive. This requires both an optical system in which the illumination light does not adversely affect the cells, and a system that can provide heating and gas exchange to maintain cells in a viable condition.

Multiplexing has enhanced the value of systems by increasing throughput. For example, the detection of a number of different fluorescent dyes at a single location allows a number of different assays to take place at a single location. An optical system which is able to increase multiplexing would save time and allow efficient use of samples and other resources.

SUMMARY OF THE INVENTION

In a first embodiment of the invention, a system is designed including an illumination source which directs illumination light through a filter and onto a sample substrate on a stage. The stage is mounted on a motorized XYZ axes carrier. Emitted fluorescence is collected by an objective lens held on an objective lens mount. The objective lens mount holds at least two objective lenses that may be selectively positioned to collect the emitted light. The collected light is collimated by the objective lens. The parallel rays of the collimated collected light beam passes through an emission filter on an emission filter wheel. Light which passes through the emission filter impinges upon an imaging lens held on an imaging lens mount. The imaging lens focuses the image onto an area array detector. The area array detector may be a CCD or alternatively may be a CID detector, a CMOS detector, or a photodiode array.

The magnification is a function of the combination of the objective and imaging lens. The objective lens mount and the imaging lens mount each hold more than one lens allowing the selective positioning of an alternative objective or imaging lens. The number of different magnifications is equal to the number of imaging lenses multiplied by the number of objectives lenses. The lenses are designed such that there is a region of parallel light rays between the objective and imaging lens. At this region of parallel light rays, the emission filter is positioned. The objective and imaging lenses are selected to be symmetrical. The symmetrically selected lens pair allows greatly reduced distortion, coma, and lateral color.

This system may include an arc lamp as the illumination source. The illumination light may be concentrated using a condenser lens. In addition, the light may be brought to the sample, on the sample holding stage, using optical fiber(s). The use of a bifurcated optical fiber cable allows illumination of the sample from two sides, producing a more uniform illumination of the sample. The illumination light may be used with an illumination filter to filter the illumination light to wavelengths within a selected wavelength range. The array detector may be a charge coupled diode (CCD) detector or may a CID detector, a CMOS detector, or photodiode array.

The emission filter used in the system may be mounted on a holder that may be selectively moved to place alternate filters in the path of the collected light. The sample holding stage may be mounted on a motorized XYZ axes, preferably allowing 1 micron incremental movements.

In addition the system may include an autofocus system in which the system automatically focuses on a desired target of interest. In one embodiment this autofocus system includes a laser directed onto a reflective substrate held on the sample holding stage and a detector including a segmented detector. Reflective light is detected by a specific detector segment on the array detector. This will indicate the positioning of the substrate. From a single detection event, this autofocus method allows relocation of the substrate to a desired location.

Such a system may use off-axis illumination. By selecting a specific condenser lens, for example by mounting the condenser lens on a wheel, the illumination spot is matched to the field of view corresponding to a given magnification. While this is not necessary for the system to function, it is more efficient and leads to higher detection sensitivity. As used herein, this is referred to as variable field illumination.

A second embodiment includes a dual detector system. In the system illumination light is again directed onto a transparent sample holding substrate on a stage. On a first side of the substrate a first objective lens collects emitted light, collimates the emitted light and directs the parallel rays of the collimated light beam through an emission filter. The emission filter may be held on a mount that allows a number of different filters to be selectively positioned in the path of the collected light. Light transmitted through the filter impinges upon an imaging lens, which focuses the collected light onto a first detector. On the opposite side of the substrate, emitted light is collected by a second objective lens and is collimated and directed through a second filter. Light transmitted through this filter impinges upon a second imaging lens that focuses the light onto a second detector. The detectors are linked to a single processor. The processor varies the signal integration from the detectors such that one detector has a relatively shorter integration interval than the other detector. This embodiment may be combined with the previous embodiment allowing for a range of magnifications for at least one of the two detectors.

In a third embodiment, an optical system for optical activation of discrete targets is disclosed. This system includes an illumination source which directs an illumination beam onto a target substrate held on a stage. The illumination light excites fluorescence from targets on the stage. The emitted fluorescence is collected by an objective lens which directs the collected light through a optical filter onto an imaging lens. The imaging lens focuses the collected illumination light onto an area array detector. The array detector is linked to a processor that identifies the locations of specific target locations. The processor then signals a spatial light modulator. This device may be an array of reflectors (digital micro-mirror device) that may be angled to direct an optical activation light beam onto specific locations on the substrate. The optical activation light beam releases caged reagents at specific locations on the substrate. These reagents may then react with compounds on the substrate. An optical effect of such a reaction may be subsequently detected by the detection system.

BEST MODE FOR CARRYING OUT THE INVENTION

The first embodiment is specifically directed to providing an optical detection system capable of providing multiple magnification levels using an efficient design that minimizes optically degrading effects from the lenses. One version of this embodiment achieves this aim by having, fixed position objective and imaging lenses. This configuration fixes magnification of an image on the detector, simplifying image processing. In this version, system focusing would be effected by moving the stage along the z-axis.

Such a system would allow for detection of a variety of biological samples including gels, DNA arrays, ordered cell arrays, disordered cell arrays, and blots. The system could accept a variety of sample formats, including samples in gels, on glass slides, or in a microplate well. If a system is able to analyze such a range of targets the required range of resolutions would be broad, from sub-micron to millimeter. This requires a thousand-fold change in magnification.

One possible approach to obtain a range of magnifications would be to design a zoom lens. However, the generally poor numerical aperture of zoom lens would make the system less sensitive. In addition the zoom lens would not have fixed magnification, but continuously variable magnification. This would make tiling of views into one mosaic image much more difficult because each view could have a different magnification. A further limitation is that even a well designed zoom lens would not be able to achieve a thousand-fold change in magnification.

Figure 1:
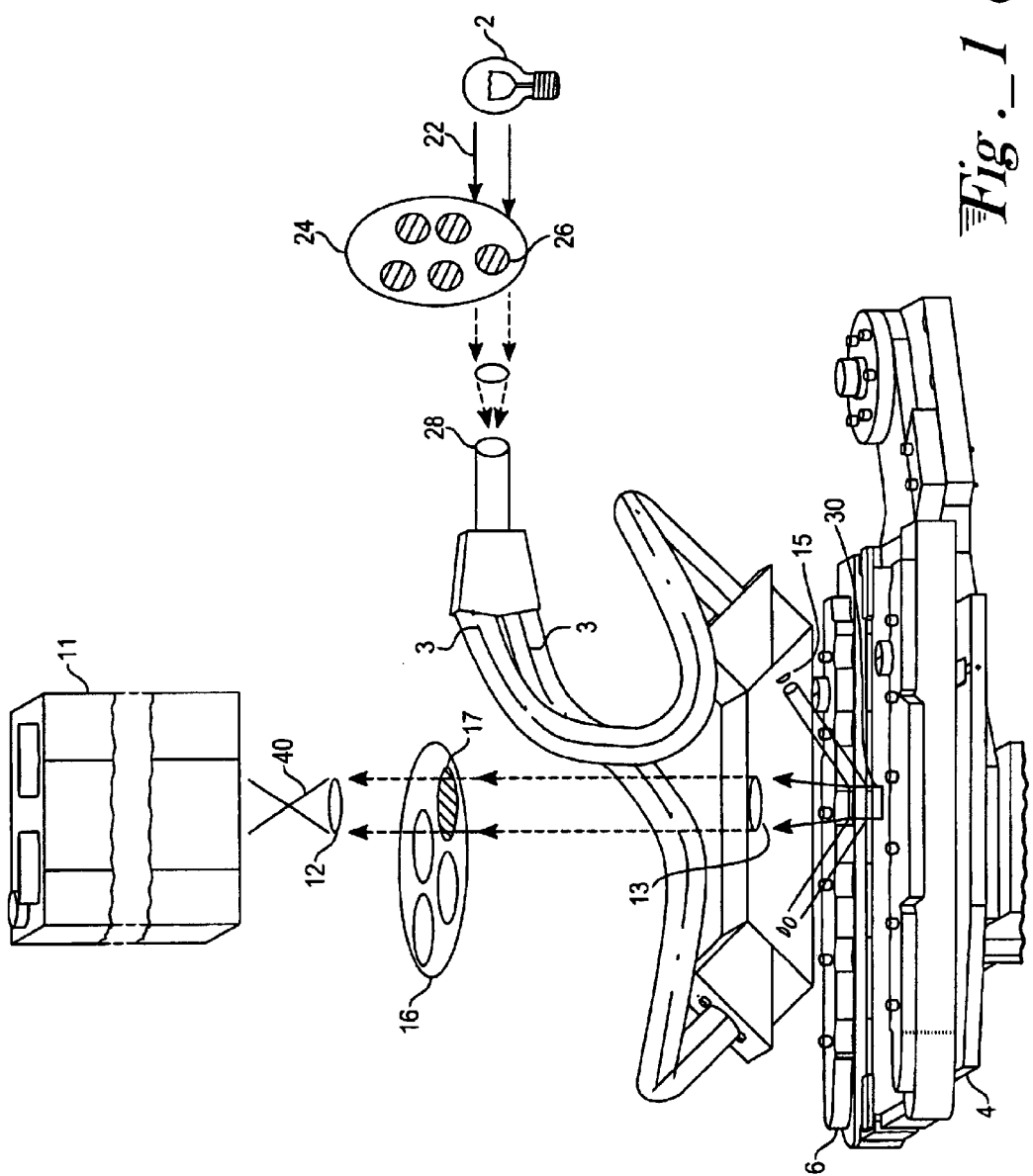
FIG. 1 is a front view of a prior art imaging device.
Figure 2:
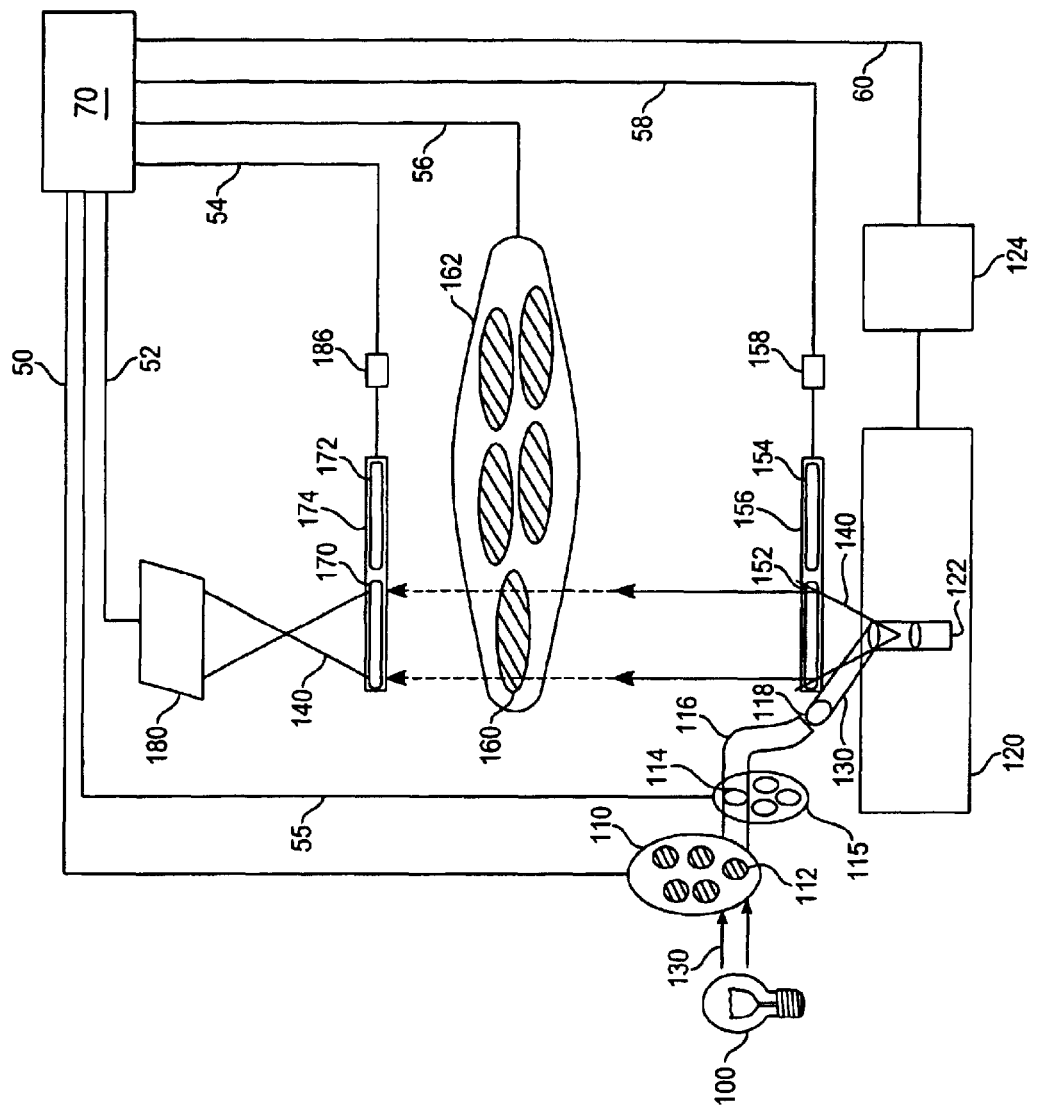
FIG. 2 is a plan view of an optical analysis system embodiment of the present invention in which a number of magnifications are obtainable.

With reference to FIG. 2, an illumination source 100 produces an illumination beam 130. Illumination source may be a broad spectrum light source such as an arc lamp. The illumination beam 130 is directed through filter 112 on filter wheel 110. Filter 112 allows selection of a desired illumination wavelength range. This illumination wavelength range is tailored to the excitation wavelengths of targets in the sample to be illuminated. In addition, the dyes selected have an excitation wavelength and emission wavelength that are sufficiently spectrally separated to allow filtering of the illumination light from emitted light. Once the illumination beam 130 has passed through filter 112 it is directed into an opening 114 in optical fiber 116. Illumination beam 130 is transmitted through optical fiber 116 and projected from the end of optical fiber 116 into condenser lens 118. The illumination beam 130 is focused by lens 118 onto sample 122.

Condenser lens 114 is mounted in a motorized wheel 115 so that variable field illumination may be employed. The motorized wheel is controlled by controller 70 via link 55.

Sample 122 is held on stage 120. An adapter may be used to hold a number of substrates or to adapt the stage to a particular substrate. Sample 122 may be a 1 inch by 3 inch glass slide. Alternatively, the sample may have a variety of formats including a multiwell plate such as a 96 well microplate. In addition the stage may provide a surface for holding a gel, such as an acrylamide gel. A variety of adapters may be used with a stage to hold the samples at precisely defined locations. This would simplify focusing. A 20 centimeter×20 centimeter stage surface area would allow detection of most gels. If a microplate is used and detection optics are above the wells, the well sides may shade the targeted bottom. In addition, refraction from a meniscus of liquid within the well could make imaging more difficult. For multiwell plate assays, it is preferred that the illustrated optical configuration be inverted. The light would be collected from the transparent bottom of the well. It is preferred that the microplate well bottom have mechanical tolerance such that cells remain in the depth of field during imaging at cellular resolution.

The excitation beam 130 excites fluorescence from a optically labeled target on target substrate 122 producing an emission beam 140. Beam 140 is collected by objective lens 152 mounted on objective lens mount 156. Controller 158 may move mount 156, allowing a selection of either first objective lens 152 or second objective lens 154 to be moved into the path to collect and transmit light from the target substrate. Both first objective lens 152 and second objective lens 154 focus to infinity. This produces a collimated beam of parallel rays.

The collected light beam passes through a selected filter 160 on filter wheel 162. The filter 160 functions most efficiently when the light rays directed through it are parallel. Filter 160 allows selection of a specific wavelength range to be transmitted through the filter. This reduces the amount of scattered li0ght from the illumination source reaching the detectors.

Light that passes through filter 160 impinges on imaging lens 170. Imaging lens 170 focuses the collected light on area array detector 180. Imaging lens 170 is mounted on imaging lens mount 174. Imaging lens mount 174 allows either first imaging lens 170 or a second imaging lens 172 to be positioned in the path of collected light and focus the collective light onto detector 180. Controller 186 controls movement of imaging lens mount 174.

In many prior system based on microscope optics, the objective lenses in the system were developed to image viewed by a human eyes, not a wide field detector array. In the present system it is preferred that the imaging and objective lens, in addition to providing the desired magnification, provide a wide field of view that would fill the field of view of a large format CCD. Any selected lens pair would be designed to image onto an area that is at least a ⅔ inch format two dimensional array. The use of such large area detectors (1 million pixel and larger) enables imaging of an entire substrate in one view.

The magnification of the sample area is a function of objective lens and the imaging lens pair. In most imaging systems (such as a microscope) a single imaging lens is used with a number of different objective lenses. The number of different magnifications available is equal to the number of objective lenses (i.e. total number of magnification is equal to N−1, where N is the total number of lenses). A microscope having four lenses (one imaging lens and three objective lenses) would allow three different magnification levels. In contrast the present system includes two or more imaging lenses and two or more objective lenses. Two imaging lenses and two objective lenses allow for a total of four different magnification levels. If three imaging lenses and three objective lenses are used a total of nine magnification levels are possible. In any given system, the total number of magnifications possible is equal to O×I where I is the number of imaging lenses and O is the number of objective lenses. This allows for a greater range of magnification, and thus a greater range of sample types to be imaged. In this manner targets ranging from 0.2 micron target to 200 micron target (a thousand-fold range) may be imaged using a single system. Such a system could have 6 lenses providing 9 different resolutions. Resolutions spanning this range could be 223, 84, 18, 10, 7, 5, 1.7, 0.8 and 0.2 microns. The 9 resolutions have jumps of 1.5× to 4× magnifications.

The objective lens images to infinity. This imaging lens collimates the collected light beam. The parallel rays of collected light are directed through the imaging filter. The parallel light rays of the collimated beam allow the most efficient function of the emission filter, minimizing light loss and providing sharp edges for the bandpass filter.

The objective lens and imaging lens used together form a selected lens pair. The system is designed such that any of the selected objective lens and any of the selected imaging lens will be symmetrical. A symmetrical system greatly reduces coma, distortion and lateral color.

Figure 8C:
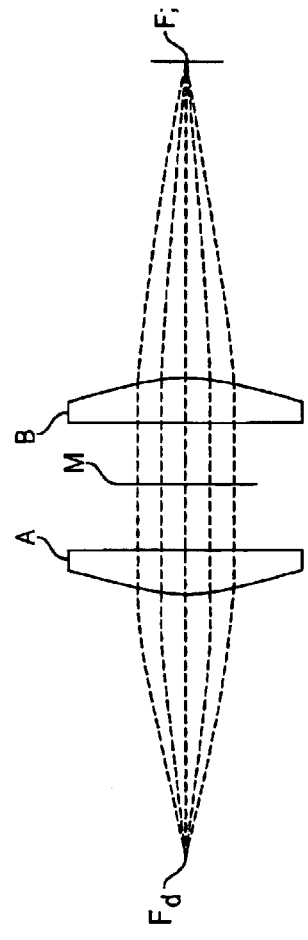
FIG. 8C is a cross-sectional view of a pair of Cooke triplet lenses.

The set of imaging and objective lenses are not adapted from existing microscopes or other optical instruments but instead designed as a set employing the required optical degrees of freedom. As such symmetrical lens design is possible. The symmetrical principle (see Warner Smith, Modern Optical Engineering, P. 372) notes that for a perfectly symmetrical lens system, coma, distortion and lateral color aberrations are identically zero. Perfect symmetry is defined by a system having 1) 1:1 magnification and 2) the elements behind the aperture stop are the exact mirror image of the elements in front of the aperture stop. This is illustrated in FIG. 8A, showing objective lens a having a focus at $F_d$ and imaging lens b having a focus of $F_i$. At the aperture stop m, elements on either side are mirror images.

Figure 8B:
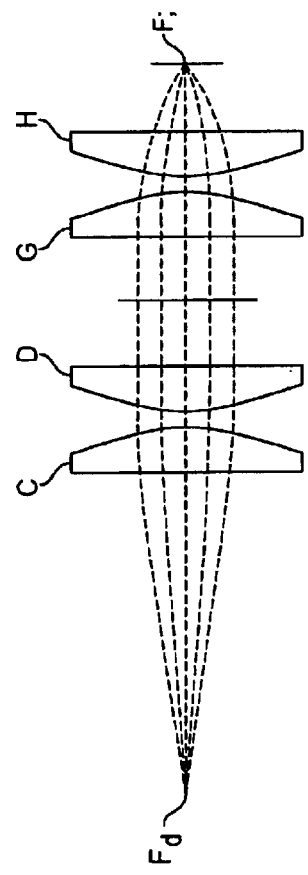
FIG. 8B is a cross-sectional view of an optically symmetrical lens pair.
Figure 8A:
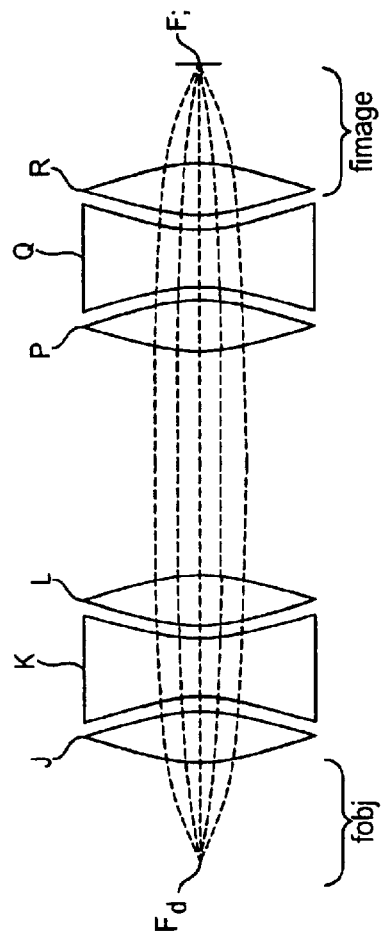
FIG. 8A is a cross-sectional view of a perfectly symmetrical lens pair.

FIG. 8B illustrates an "optically symmetrical" lens system as that term is used herein. The lens system is not perfectly symmetrical, but still minimizes coma, distortion and lateral color aberrations. In such lens systems the system has 1) 1:1 magnification or any other magnification system; 2) the same number of lens elements of the objective lens and imaging lenses; and 3) the elements behind the aperture stop are symmetrical in shape to the elements and are arranged as mirror images of each other. In FIG. 8B lens pair c,d form the objective having a focus $F_d$. Lens pair g,h form the imaging lens. Inner lens elements g,d are planoconvex lenses having a convex surface facing away from the aperture stop while outer lens elements c,h are planoconvex lenses having a convex surface facing towards the aperture stop. For lens systems that cover a wide field, such as for large format CCDs, symmetrical construction is generally required for low distortion and coma.

One type of lens that can be selected for both the objective lens and the imaging lens is a Cooke triplet. This design theoretically provides enough degrees of freedom to correct for the eight primary corrections: focal length, axial chromatic aberration, lateral chromatic aberration, petzval curvature, spherical aberration, coma, astigmatism and distortion. In addition, pairs of Cooke triplets used as objective and imaging lenses would be optically symmetrical. Each Cooke triplet would then be corrected for an infinite conjugate ratio. To a first order paraxial approximation, the ratio of the focal lengths of objective and imaging Cooke triplets would determine the magnification of the matched selected lens set.

Between the emission and objective lenses in such a lens pair would be an emission filter. This filter is located at a region of parallel light rays. In one implementation of this embodiment, the objective lenses are mounted on an objective turret mount, with each lens held on the mount such that when the lens is rotated or moved to a position to image a sample, the lens is held at its focal length distance from the target. In a similar manner the imaging lenses would be held on a mount (e.g. a turret) such that when an imaging lens was positioned to image collected light on the detector, the imaging lens would be spaced at its focal length from the detector.

FIG. 8C illustrates a pair of Cooke triplets as used in imaging. The objective triplet lens includes 3 elements, j,k,l and focuses at $F_d$, the objective focus. The imaging lens triplet p,q,r has a focus $F_i$. The imaging and objective lenses are symmetrical.

An alternative configuration could include 12 mm, 50 mm, 85 mm, or 100 mm lenses from a variety of sources. In one configuration, a low resolution lens having a 1.7× magnification is used with a high resolution lens having a 8.3× magnification. The low resolution imaging lens is a Hastings triplet having a 50 mm focal length and the low resolution objective lens is a Hastings triplet having a 85 mm focal length. The objective lens has a numerical aperture (NA) of 0.15. The high resolution objective lens is a Hastings triplet having a focal length of 12 mm and the high resolution imaging lens is Hastings triplet having a focal length of 100 mm. The high resolution objective has a NA of 0.2.

The detector 180 may be an area array CCD. A 1.3 megapixel cooled CCD provides a large imaging area, 50% quantum efficiency at the 400 nanometer light wavelength and 18000 quantum well. These chips can be cooled reducing the noise of the detector. Higher grade CCD detectors with larger pixel numbers higher quantum efficiencies and quantum wells (around 100,000 electrons) are also available. Alternate detectors include charge injection device (CID) detectors, CMOS detectors, and photodiode array detectors.

A number of the elements of the system may be controlled by a central system control. For example, in FIG. 2 illumination filter wheel 110 is linked by link 50 central system control 70. Controller 158 controlling objective lens mount 156 is linked by link 58 to system control 70. Imaging filter wheel 162 is linked by link 56 to central control 70. Imaging lens mount 174 controlled by controller 186 is linked to by link 54 to central control 70. The XYZ sample stage control 124 is linked by link 60 to system control 70. Finally, the area array detector 180 is connected by link 52 to central system control 70. A user interface allows the user to select the illumination filter, objective lens, imaging filter and imaging lens. The system control also allows an area array detector to be used in conjunction with the stage motor control to focus on a designated target. The processor may also instruct the stage motor to advance following an image capture of a sample on the stage.

In a second embodiment, the system includes two detectors that may be used in tandem. The two detectors allow for one detector to be used at long integration periods and another to be used at more rapid integration periods. Alternatively the first detector could be used for detection of cells or cell spots and the second detector used for a finer resolution intracellular imaging. Both detectors are connected to a system processor. This processor allows signal from one processor to be used to determine settings for the other processor and related optical components.

Fluorescence signal degradation can occur to photobleaching of dyes, loss of cell viability, leakage of dye molecules from the cell and compartmentalization. All of these phenomena are time dependent. Using a CCD detector or other area array detector, longer exposure integration intervals may compensate for noise from signal degradation.

Figure 3:
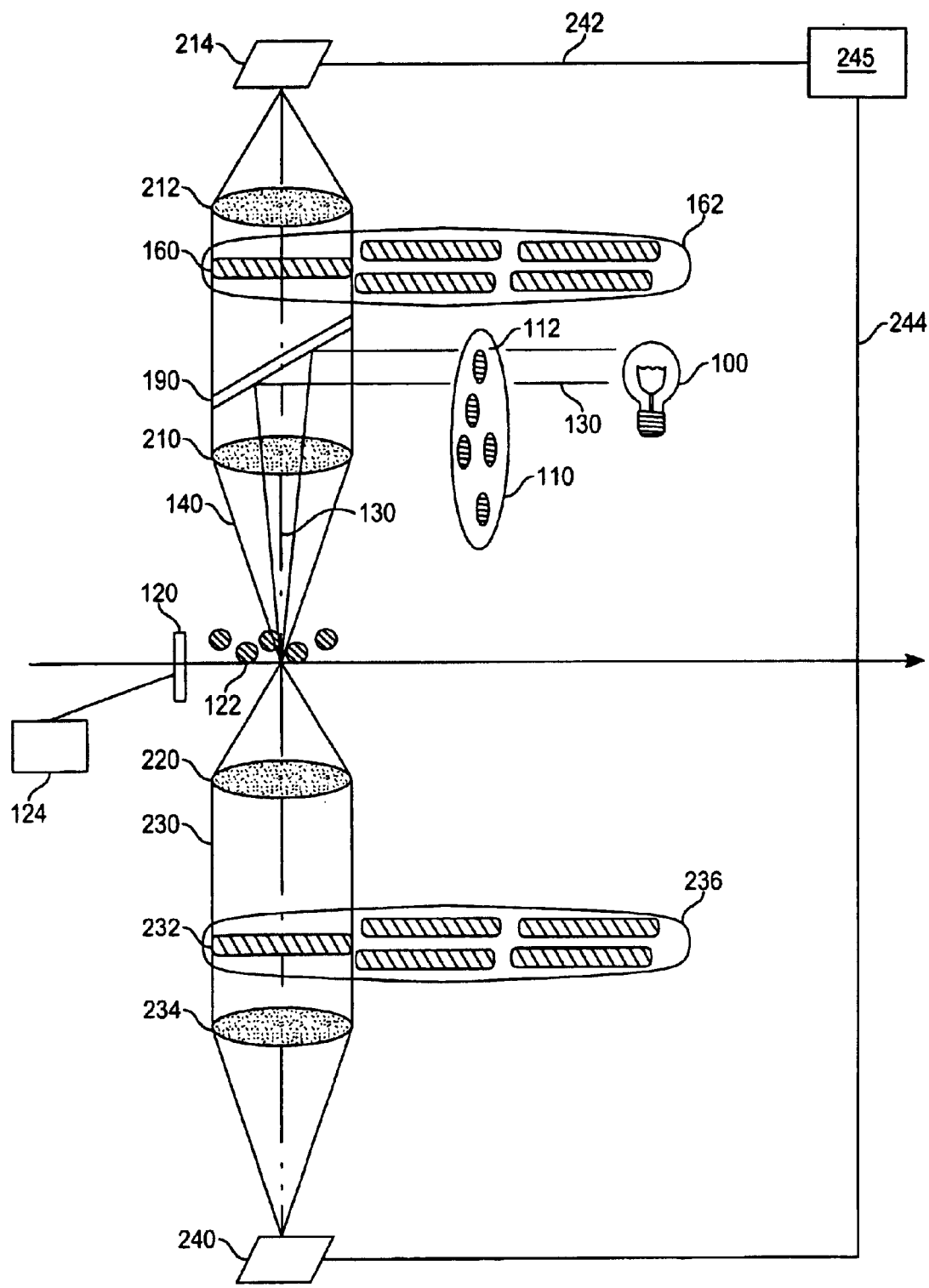
FIG. 3 is a plan view of an alternative embodiment of the present invention in which two detectors are used, the detectors allowing detection of a optical event over two different integration intervals.

One example implementing the second embodiment of the invention is illustrated in FIG. 3. In this embodiment illumination lights source 100 produces an illumination beam 130 which is directed through illumination filter 112 on illumination filter wheel 110. Illumination filter wheel 110 may be rotated to place a selected illumination filter in the pathway of the illumination beam 130. The illumination filter 112 filters out light that is not within a selected wavelength range. The illumination beam 130 passes through filter 112 and impinges on dichroic mirror 190. Dichroic mirror 190 reflects lights of the wavelength of the illumination beam 130 through objective lens 210 and onto sample substrate 122 on sample holder 120. As in the previous embodiment sample stage 120 is mechanically linked to an XYZ motor on sample stage controller 124. The sample substrate 122 is held on sample stage 120 such that the sample may be viewed from both above and below the sample.

Light emitted from both sides of the sample substrate may be collected. In this embodiment the sample substrate should be optically transparent and the sample should allow light to be collected from both sides of the sample. If a microplate is used the reagents within the microplate well should be removed such that the liquid meniscus does not distort the collected light. On the first side of the sample well the collected illumination light 140 is collected by objective lens 210. Objective lens 210 collimates the collected light. The collimated collected light beam is transmitted through dichroic mirror 190. Dichroic mirror 190 is selected such that light of the collected wavelength may pass through dichroic mirror 190. The collected light beam passes through emission filter 160 on emission filter wheel 162. This emission filter is selected by user to filter out wavelengths other than wavelengths within the range of emission wavelengths from the target. The collected light beam 140 after passing through filter 160 impinges upon imaging lens 212. Imaging lens 212 focuses the collected light onto area array detector 214. Detector 214 is connected to processor 245 by link 242.

Light emitted from the bottom of sample substrate 122 is collected by a bottom objective lens 220. Objective lens 220 collimates the collected light into beam 230. Collected light beam passes through filter 232 on filter wheel 236. Filter 232 filters out wavelengths other than wavelengths within a selected range. After passing through filter 232 the collected light beam impinges upon imaging lens 234. Imaging lens 234 then focuses the collected light on second area array detector 240. The second array imaging detector 240 is linked by link 244 to processor 245.

The dual detector embodiment shown in FIG. 3 allows for dual integration of light collected from a sample. The first area array detector 214 may be used for short integration time image capture. This high speed imaging is useful for kinetic measurements. At the same time the rapid integration measurement is taking place a longer integration interval may be used on the second detector 240. The longer integration time increases the sensitivity of the measurement, allowing for detection of fewer detectable labels on the target.

One variation of the two detector imaging embodiment is the design of detector to allow imaging at a first resolution and a second detector to allow imaging at a second resolution. For example, objective and imaging lens combination 210 and 212 could provide a relatively low resolution imaging of 2 microns or greater for cell detection by detector 214. Objective and imaging lenses 220 and 234 could provide a relatively high resolution imaging of 1 micron or less to allow for intracellular imaging. As a cell was detected by a first detector, the processor could analyze corresponding signal from the second detector to detect targets inside the cell. Such detection could occur in real time, allowing for kinetic assay of cellular targets.

In the third major embodiment, the disclosed optical system includes a means for activating an optically activatable sample at a discrete locations. The system has an optical system for analysis of a sample. The sample includes a region including photo-activatable compounds. The system includes a means for activating the photo activatable compounds.

A large number of optically activated probes are commercially available. The Handbook of Fluorescent Probes and Research Chemicals, Richard Hausland, 6$^{th}$ Ed. (Molecular Probes, Eugene Oreg.) (1996) lists a number of photo-activatable or "caged" reagents. The release of these compounds may be spatially and temporally controlled. In addition, the chemical caging process may make the caged compound membrane permeable. The available caged compounds include nucleotides, phosphates, chelators, ionophores, secondary messengers, analogs of bioactive molecules, neurotransmitters, pharmaceuticals, fluorescent dyes and aminoacids. These compounds are caged using a caging moiety that is detached by flash photolysis at ≦360 mm illumination for microseconds to milliseconds. A number of caging groups are available.

Figure 4:
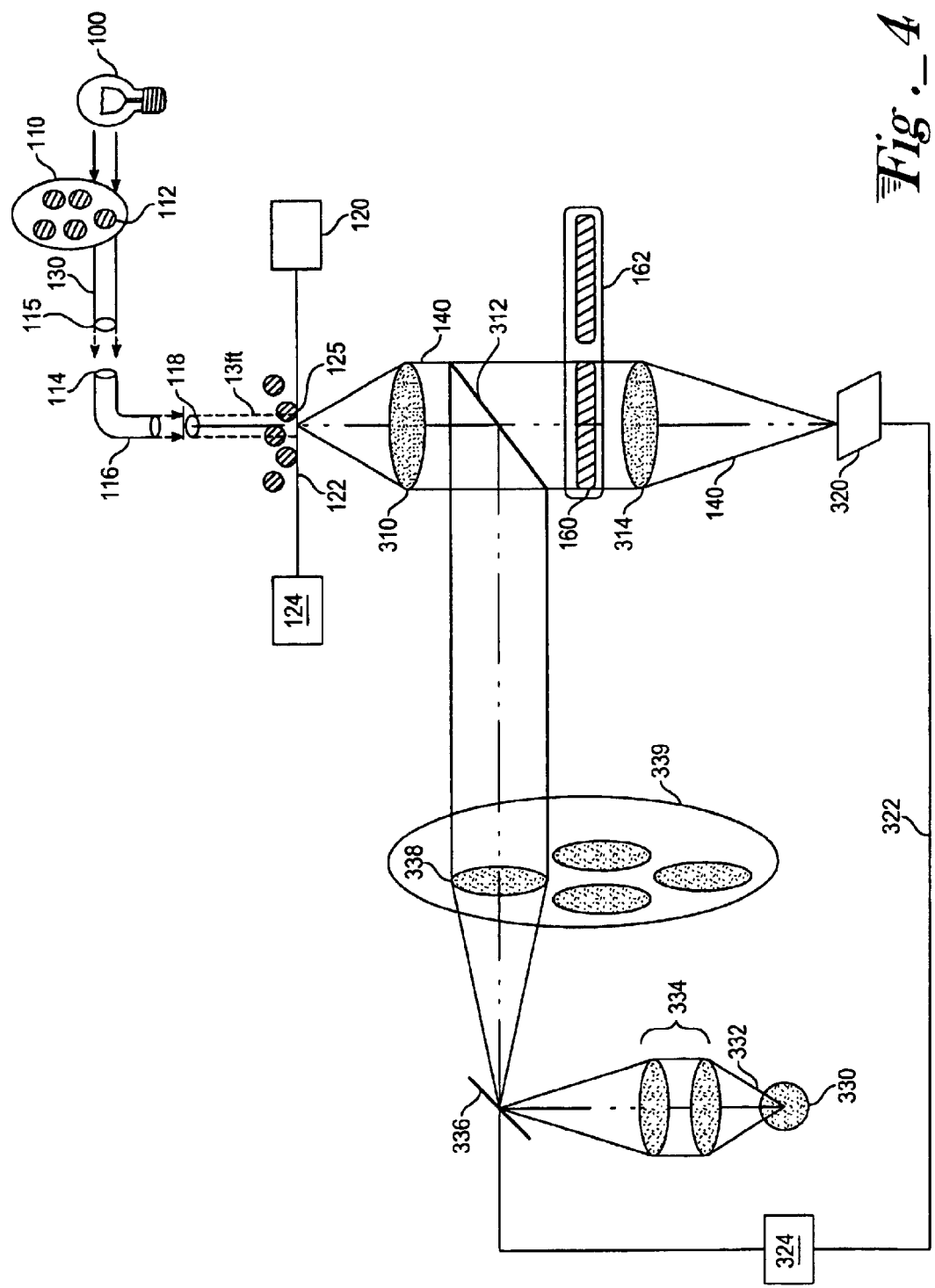
FIG. 4 is a plan view of an alternative embodiment in which an optical activation system is used.

With reference to FIG. 4 an illumination source 100 directs an illumination beam 130 through a illumination filter 112 on illumination filter wheel 110. The illumination beam 130 passes through illumination filter 112 and is focused by focusing lens 115 into end 114 of optical fiber 116. The illumination light travels through optical fiber 116 and is emitted from the end of optical fiber 116. The illumination light is condensed by condenser lens 118 and directed onto target 125 on sample substrate 122. Substrate 122 is held on stage 120. Stage 120 may be moved in along 3 axis by controller 124. Emitted light excited by illumination beam 130 is collected by objective lens 310. The collected light beam 140 is collimated and directed onto beam splitter 312. The light of the wavelength of the collected emitted light passes through beam splitter 312 and passes onto emission filter 160 on filter wheel 162. The selected wavelengths pass through filter 160 onto imaging lens 314. Imaging lens 314 focuses collected light beam 140 onto detector 320. Detector 320 is linked by electronic link 322 to processor 324. The processor 324 may identify discrete locations of targets of interest. Such targets may be an array spot, a cell on a cell array, a cell or bead on a substrate, or some other discrete target.

A secondary light source 330 produces a beam of optical activation light 332. This optical activation light beam has properties which allow the light beam to optically activate caged compounds on the substrate. Such photo-activated compounds are then able to react with targets on the substrate. In this way a second assay may be performed at the location of an initial assay. Flash photolysis of a photo activatible or "caged" probe is one method of controlling the release reagents at a specific location. The caged compound may be detached in a period of microseconds to milliseconds by flash photolysis. For example, a number of compounds have been caged with components which release the reagent upon exposure to UV light.

In the embodiment of FIG. 4, the optical activation beam 332 is directed through a condenser lens 334 and onto spatial light modulator 336. U.S. Pat. No. 6,483,641 discloses one application of a spatial light modulator. The term "spatial light modulator" as used herein refers to all such spatial light modulators able to selectively transmit an array of transmission light pixels to selectively illuminate a target. Such a pixilated light array may be formed by a number of devices including an array of ferroelectric liquid crystal devices, digital micro-mirror devices, and electrostatic microshutters. U.S. Pat. No. 5,587,832 discloses some of these devices. This device allows optical activation beam 332 to be reflected as a number of localized illumination beams. These are reflected through relay lens 338 and onto dichroic mirror 312. Dichroic mirror 312 directs the optical activation beam through objective lens 310 and onto sample substrate 122. At spot location 125, a caged compound could be activated by the optical activation light. Processor 324 is linked to spatial light modulator 336 such that the controller may send signals directing the spatial light modulator to illuminate only specific localized areas. The uncaged reagents may then interact with a cells, beads, or bound compounds. The results of the reaction could then be detected, as by optical detection. A subsequent or continuous imaging of the sample could indicate the reaction has occurred or determine the effect on a sample component.

Relay lens 338 is selected by rotating motorized wheel 339. Thereby variable field illumination can be employed by the activation beam.

Figure 5:
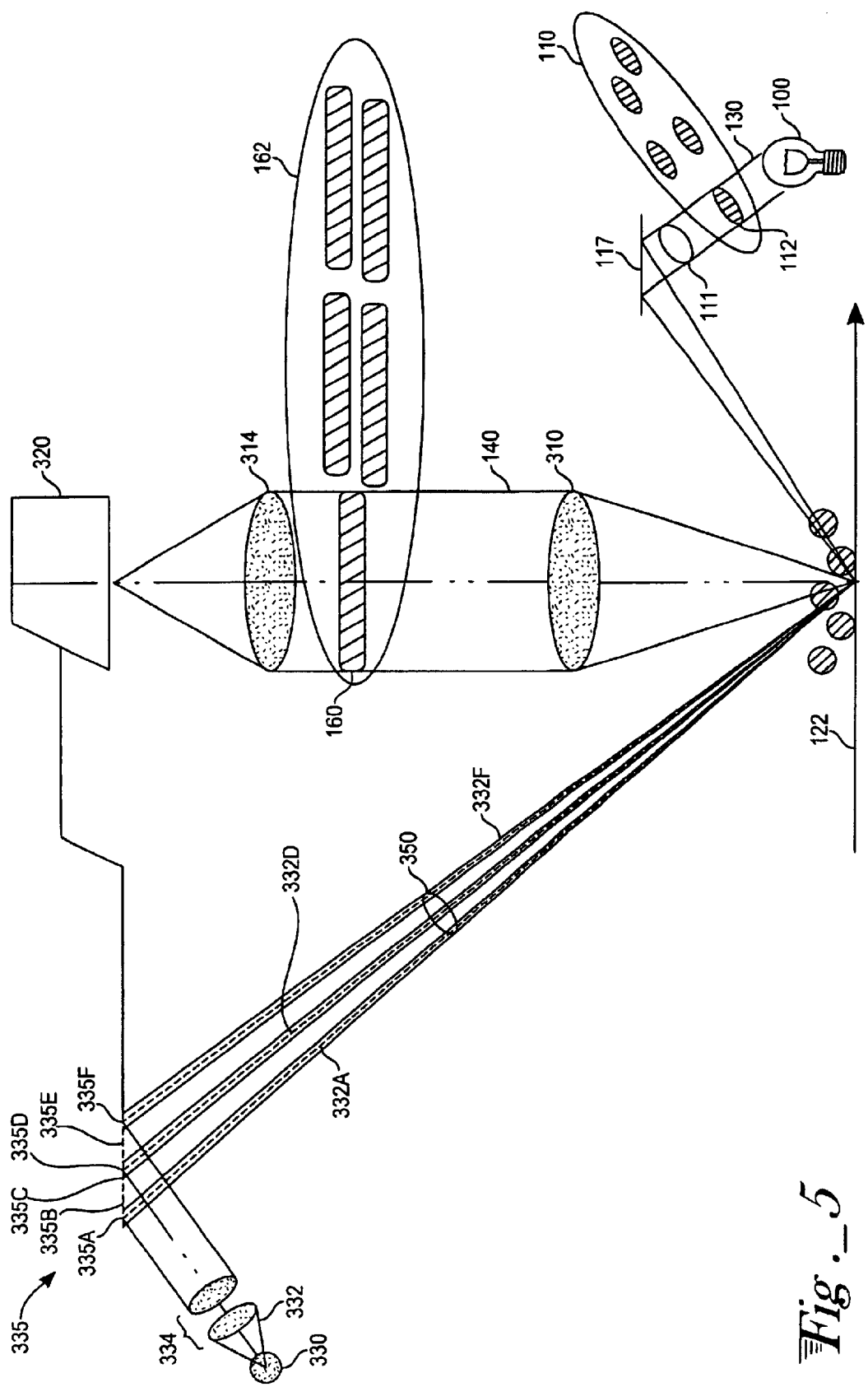
FIG. 5 is a plan view of an alternative embodiment of an optical activation light system.

Another alternative embodiment of the optical activation system is illustrated in FIG. 5. Again an illumination light source 100 produces an illumination beam 130 directed through an optical filter 112 on filter wheel 110. The illumination beam is directed through a condenser lens 111 and reflected by mirror 117 onto sample substrate 122. Emitted light is collected by objective lens 310. This light is collimated and directed through emission filter 160 and onto imaging lens 314. Imaging lens 314 focuses the collected light onto an area array detector 320. Again the image from array detector 320 is processed by a processor (not shown).

Light source 330 produces an optical activation beam 332 which passes through condenser lens 334 and onto a digital micro-mirror device. The digital micro-mirror device is composed of reflectors 335A–33F. Such reflectors are positioned in a 2 dimensional array. Each reflector may be separately angled to direct a light beam. Optical activation light beams 332A, 332D, and 332F are directed by respective reflectors 335A, 335D and 335F through relay lens 350 to specific locations in sample substrate 122. As in FIG. 4, the optical activation beam optically releases a reagent which subsequently reacts with the illuminated targets (e.g. cells, beads, or array spots). The reaction is optically detectable by the previously described illumination and detection system.

It will be appreciated that a number of the described embodiments can be used together in a combined system. For example, one embodiment disclosed a system having a range of magnifications utilizing symmetrical objective and imaging lens selected as a pair. This system configuration may be used with a system in which an additional detector is used. This would combine the systems shown in FIGS. 2 and 3 allowing both a range of magnification and a single system along with varied integration periods of the detected signals. The system of FIG. 2 could also be combined with an optical activation system such as a system shown in FIGS. 4 and 5. In these systems the configuration shown in FIGS. 4 and 5 could be amended such that a plurality of selectable objective and imaging lens are used in the system. It would also be possible to combine the elements of the system of FIG. 3 with the optical activation systems of FIGS. 4 and 5. In such a system dual detectors would allow rapid integration period of short integration intervals. At a selected target location the caged compounds could be optically activated by an optical activation beam directed to localized areas.

Finally, it is envisioned that all three features can be combined in a single system that would allow for range of magnifications, integration over short or relatively longer time intervals, and optical activation of caged probes or reagents to allow deeper multiplexing.

A number of different features may be used with any of the described embodiments.

Cell Viability

For cell array assay, ideally the cells should remain alive. This allows for reassay of the cells as well as kinetic measurement of cell function. A number of features may be added to the present system to allow for cell viability. First a fluidic manifold may deliver fluid to live cells to feed the cells or provide the cell nutrients required for the cells to remain viable. In addition a heating element may be used with the cells to maintain the cells at a desired temperature. Finally the cells may be enclosed to prevent loss of water resulting in cell dehydration. U.S. Pat. No. 6,365,367, hereby incorporated by reference, discloses a device for holding specimens that includes a gas flow control and a heated lid. Such a device could be used to maintain cells during analysis.

Autofocus

Although the system described in the previous figures could be manually focused the automatic focus is preferred. Such automatic focus reduces focusing time and aids in focusing accuracy. Prior systems use detection of fluorescence (e.g. from the sample targets) to focus the system. A sample would be held stationary as the objective lens was moved closer or further from the sample. An initial detection of fluorescence by the detector indicated system focus within a sample. Such autofocus methods are described in U.S. Pat. Nos. 6,573,039 and 6,130,795. However, moving the objective lens alters the magnification. Focusing by Z axis stage movement would eliminate the change in magnification and resultant image stitching problems inherent in devices that are focused by objective movement.

A laser autofocus system would be more rapid than other focus systems used in imaging instrumentation. One such system is disclosed in U.S. Pat. No. 6,441,894. The above systems require scanning through a number of points. The detected fluorescence is fit to a curve to determine an optimal focus. This scanning and signal processing is time consuming and the focusing process can take several times longer than acquiring the image itself.

Figure 6:
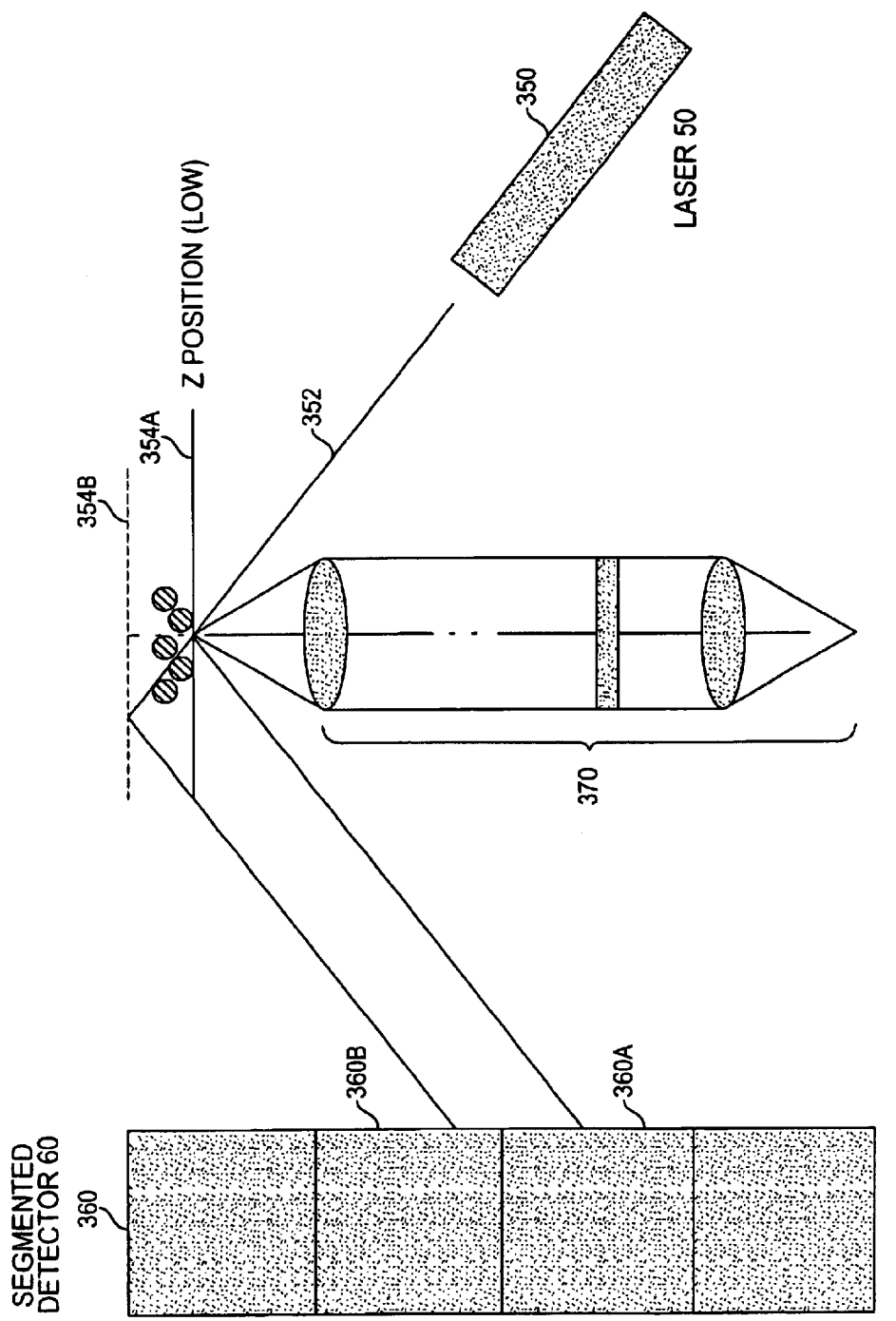
FIG. 6 is a plan view of an autofocus system that may be used with any of the embodiments shown in FIGS. 2–5.

An alternative is a system using a laser and a linear segmented detector which requires only a single data point to focus on a surface. In FIG. 6 laser 350 produces laser beam 352 directed onto sample substrate surface 354A. The coherent laser beam 352 reflects from surface 354A at an angle equal to the angle of incidence. This reflective light is reflected to a segmented detector 360. Such an detector may be a linear CCD detector. When the reflected light is detected at segment 360A on segmented detector 360, this indicates that the substrate is positioned in focus for optical analysis by optical elements 370. These elements include an objective lens, an imaging filter, an imaging lens, and a detector. Illumination optics are not shown.

When the substrate is at a different position the reflected laser light will be detected by a different segment of the segmented detector. Dashed line 354B indicates a substrate positioned at a position that would be out of focus for the optical system. Laser beam 352 reflects from a different location on substrate 354B and thus is detected by a different segment 360B on segment detector 360. This indicates to the system processor both the direction required to move the substrate to bring the substrate into focus and the amount of movement needed to bring the substrate into focus. In this manner a single laser illumination and detection is all that is required to know both the direction required to move the substrate to focus the substrate and the distance to move the substrate to focus.

System Processing

Figure 7:
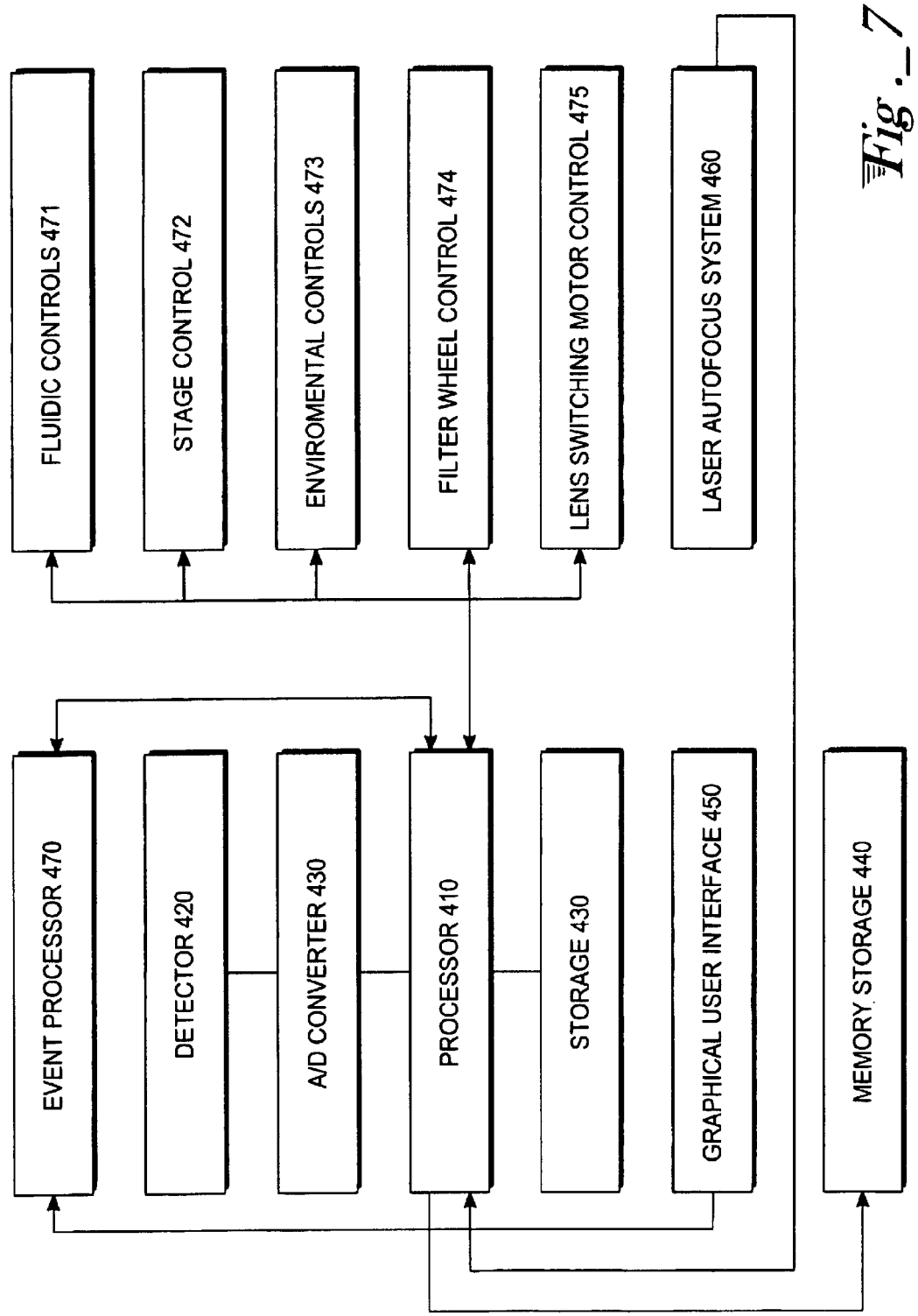
FIG. 7 is a flow chart illustrating system function.

FIG. 7 illustrates a flow diagram of the processing and control of the system. Detector 420 detects light from the substrate and records this detection as an array of signal intensity levels. This is sent to analog digital converter 430 that converts the measured signal into digital data. The digital data is sent to the processor 410. The processor 410 may transfer converted data to a memory storage 440.

A graphic user interface 450 may also be used to instruct the event processor 470 allowing manual selection of system set up or event processing. The event processor relays this instruction to the processor 410.

A laser autofocus system 460 is used to determine in a single detection event the required movement of the stage that brings the stage into focus. This information is relayed to processor 410 which signals stage control 472 to move to stage along the Z axis until the substrate is in focus.

The processor 410 is electronically linked to a number of system elements including the filter wheel control 474 and the lens switching motor control 475. This allows either user selected or system selected choice of illumination and emission filters and objective and imaging lens. The process may also send electronic signals to fluidic controls 471 and environmental control 473. These signals could be in response to either user commands or detection events.

The event processor can be either an additional physical processor or a "virtual processor", an application running on a system processor. This processor analyzes the data stream. Signals from detected targets may automatically trigger system setting adjustments, including control of fluidics and environmental controls, change in stage positioning (including advancing X-Y position of the stage following image acquisition), lamp control, filter wheel switching and/or lens switching.

Imaging Processing

Detection of kinetic events requiring multiple images to be recorded over time may be taxing on processing and data storage resources. A number of adaptations may aid in imaging image processing. The event processor may be programmed to store only the changes from one image to the next in a series (rather than the image themselves) reducing data storage requirements. The processor could also stitch multiple images into a single mosiac.

What is claimed is:

1. A system for optical analysis of targets comprising:

an illumination source producing an illumination beam;

a stage for holding a sample onto which said illumination beam is directed;

a first objective lens collecting light from said sample and transmitting said light as a collected light beam;

a first imaging lens that receives collected light from said objective lens and focuses said collected light;

a first area array detector positioned to detect collected light focused by said first imaging lens;

a second objective lens collecting light from said sample and transmitting said light as a collected light beam;

a second imaging lens that receives collected light from said objective lens and focuses said collected light;

a second area array detector positioned to detect collected light focused by said first imaging lens;

a processor that simultaneously integrates signals from said first and said second detector, wherein said processor integrates a signal from a first detector for a first time interval and said processor integrates a signal from said processor for a second time interval, wherein said first time interval is shorter than said second time interval.

2. The system of claim 1, wherein said first area array detector and said second area array detector are selected from a group comprising CCD detectors, CID detectors, CMOS detectors, and photodiode array detectors.

3. The system of claim 1, wherein said illumination source is an arc lamp.

4. The system of claim 3, wherein the illumination beam is directed by an optical fiber onto the sample.

5. The system of claim 1, further comprising an illumination filter placed in the path of the illumination light.

6. The system of claim 5, further comprising an illumination filter holder that allows one of a plurality of illumination filters to be positioned in the path of the illumination light.

7. The system of claim 1, wherein the first and second area array detectors are selected from the group consisting of a CCD detector, a CID detector, a CMOS detector or a photodiode array detector.

8. The system of claim 1, wherein said sample holding stage may be selectively moved along a z-axis.

9. The system of claim 1, further including an autofocus system.

10. The system of claim 9, wherein said autofocus system includes a laser directed onto a reflective substrate on the sample holding stage, an array detector positioned to detect the reflected light, and a processor, wherein said processor determines the focus on the substrate by the location on the array detector to which reflected light is detected.

11. The system of claim 1, wherein said stage includes an adapter held on said stage.

* * * * *